United States Patent [19]
Carey et al.

[11] Patent Number: 5,378,372
[45] Date of Patent: Jan. 3, 1995

[54] CONTROL OF SCALE FORMATION IN AQUEOUS SYSTEMS

[75] Inventors: William S. Carey, Ridley Park; Andrew Solov, Holland; Donald T. Freese, Glenside; Libardo A. Perez, Morrisville, all of Pa.

[73] Assignee: Betz Laboratories, Inc., Trevose, Pa.

[21] Appl. No.: 74,254

[22] Filed: Jun. 9, 1993

[51] Int. Cl.$^6$ ............................................. C02F 5/14
[52] U.S. Cl. ................... 210/697; 210/698; 210/699; 210/701; 252/180; 252/181
[58] Field of Search ................ 210/696–701; 252/180, 181

[56] References Cited

U.S. PATENT DOCUMENTS

| | | | |
|---|---|---|---|
| 3,776,850 | 12/1973 | Pearson et al. | 252/89 |
| 4,654,159 | 3/1987 | Bush et al. | 252/95 |
| 4,659,481 | 4/1987 | Chen | 210/697 |
| 5,062,962 | 11/1991 | Brown et al. | 210/698 |
| 5,116,513 | 5/1992 | Koskan et al. | 210/698 |
| 5,152,902 | 10/1992 | Koskan et al. | 210/698 |
| 5,183,590 | 2/1993 | Carter et al. | 252/392 |
| 5,248,438 | 9/1993 | Perez | 210/698 |

FOREIGN PATENT DOCUMENTS 293156 10/1990 Japan .

*Primary Examiner*—Peter A. Hruskoci
*Attorney, Agent, or Firm*—Alexander D. Ricci; Richard A. Paikoff

[57] ABSTRACT

A method and polymers for inhibiting the formation of scale is disclosed. The method is particularly effective at inhibiting the formation and deposition of calcium scales in circulating aqueous systems such as cooling water systems. The method comprises introducing into the aqueous system a polymer of the general formula:

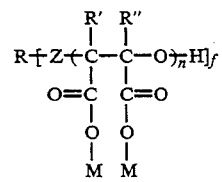

wherein R is hydrogen, alkyl, aryl, substituted alkyl or substituted aryl; R' and R" are each independently hydrogen, $C_{1-4}$ alkyl or $C_{1-4}$ substituted alkyl; Z is O, S, NH, or NR, where R is as described above; n is a positive integer greater than 1; f is a positive integer; and M is hydrogen, a water soluble cation (e.g., $NH_4^+$, alkali metal), or a $C_1$–$C_3$ alkyl group.

15 Claims, No Drawings

CONTROL OF SCALE FORMATION IN AQUEOUS SYSTEMS

FIELD OF THE INVENTION

The present invention relates to the treatment of water to inhibit the formation of scale. More particularly, the present invention relates to the use of a modified polyepoxysuccinic acid to inhibit scale formation in aqueous systems.

BACKGROUND OF THE INVENTION

Although the present invention has general applicability to any given system where the formation and deposition of calcium scale and in particular calcium carbonate scale is a potential problem, the invention will be discussed in detail as it concerns cooling water systems. The present invention relates to methods for inhibiting scale deposits in aqueous systems.

In industrial cooling systems, water such as from rivers, lakes, ponds, etc., is employed as the cooling media for heat exchangers. Such natural waters contain large amounts of suspended materials such as silt, clay, and organic wastes. The cooling water from heat exchangers is typically passed through a cooling tower, spray pond or evaporative system prior to discharge or reuse. In these systems, the cooling effect is achieved by evaporating a portion of the water passing through the system. Because of the evaporation which takes place during cooling, suspended materials in the water become concentrated. Fouling materials from the feedwater or as a result of evaporative concentration can settle in locations of low flow rate and cause corrosion and inefficient heat transfer. Agglomerating agents such as polyacrylamides and polyacrylates have been used to agglomerate fine particles of mud and silt into a loose floc for removal. However, these flocs tend to settle in cooling tower basins and frequent cleaning is necessary to remove the settled flocs from the tower basins.

The water employed in industrial cooling water systems also often contains dissolved salts of calcium and magnesium, etc., which can lead to scale and sludge deposits. One of the most common scale deposits in cooling water systems is calcium carbonate. It normally results from the breakdown of calcium bicarbonate, a naturally occurring soluble salt. Calcium carbonate has a relatively low solubility and its solubility decreases with increasing temperature and pH. Thus, the rate of calcium carbonate deposition increases with increasing pH and temperature.

Deposit control agents such as phosphates, phosphonates and polyacrylates are often used to inhibit calcium carbonate scale formation in industrial cooling water systems. The use of polyacrylates alone is not effective at high calcium concentrations because undesirable polyacrylate-calcium precipitates are formed reducing efficiency.

Although phosphonates are very effective at controlling calcium carbonate scale formation, and certain phosphonates exhibit excellent calcium tolerance, i.e. the ability to inhibit calcium carbonate scale in water having a propensity toward scale deposition, they can produce insoluble phosphonate - calcium complexes or calcium phosphate scale upon degradation, especially in waters having high calcium concentrations and pH. Further, current limits on total phosphorus discharge (as P) due to environmental concerns limit the acceptability of the use of phosphonates for water treatment.

Preventing the corrosion and scaling of industrial heat transfer equipment is essential to the efficient and economical operation of a cooling water system. Excessive corrosion of metallic surfaces can cause the premature failure of process equipment, necessitating downtime for the replacement or repair of the equipment. Additionally, the buildup of corrosion products on the heat transfer surface reduces efficiency, thereby limiting production or requiring downtime for cleaning. Reduction in efficiency will also result from scaling deposits which retard heat transfer and hinder water flow.

Scale can also cause rapid localized corrosion and subsequent penetration of metallic surfaces through the formation of differential oxygen concentration cells. The localized corrosion resulting from differential oxygen cells originating from deposits is commonly referred to as "underdeposit corrosion".

SUMMARY OF THE INVENTION

The present invention provides an effective method and novel polymers for inhibiting scale formation in aqueous systems. The present invention is effective at conditions of high pH, high calcium concentration and high M-alkalinity where conventional treatments lose efficacy. The treatment of the present invention also controls calcium scale formation without forming undesirable inhibitor-calcium precipitates. Also, the method of the present invention does not employ phosphorus, thereby reducing or eliminating the undesirable discharge of phosphorus-containing compounds. The method of the present invention allows industrial cooling water systems to operate at higher cycles of concentration, acid feed for pH control can be reduced or eliminated, and phosphorus limited systems can be treated effectively. In addition to treating waters having high calcium levels, the present invention is also effective at treating waters having low levels of calcium.

The method of the present invention comprises treating industrial waters with a modified poly[epoxysuccinic acid] of the general formula:

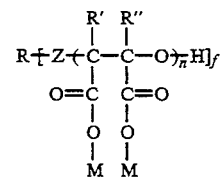

wherein R, when present, is H, a substituted or non-substituted alkyl or aryl moiety having a carbon chain up to the length where solubility in an aqueous solution is lost, or a repeat unit obtained after polymerization of an ethylenically unsaturated compound; R' and R" are hydrogen, $C_{1-4}$ alkyl or $C_{1-4}$ substituted alkyl; Z is O, S, NH, or NR, where R is as described above; n is a positive integer greater than 1; f is a positive integer; and M is hydrogen, a water soluble cation (e.g., $NH_4^+$, alkali metal), or a non-substituted lower alkyl group having from 1 to 3 carbon atoms. (When R is not present, Z may be $MO_3S$, where M is as described above).

In a preferred embodiment of the invention, R is a $C_1$-$C_{20}$ alkyl or substituted alkyl moiety, or a $C_4$-$C_9$ aryl or substituted aryl moiety, R' and R" are hydrogen, Z is NH, n is greater than 1, f is 1-2, and M is $Na^+$.

In a particularly preferred embodiment of the invention, R is a —CH$_2$C$_6$H$_4$CH$_2$ moiety, R' and R" are hydrogen, Z is NH, n is greater than 1, f is 2, and M is Na$^+$.

In the present invention, the modified poly[epoxysuccinic acids] are added to the aqueous system at substoichiometric levels to inhibit scale formation. The method of the present invention provides effective calcium carbonate deposition inhibition in waters having relatively high Langelier saturation indexes. The method of the present invention provides such control at relatively low active treatment levels without the use of phosphates or phosphonates.

DESCRIPTION OF THE PREFERRED EMBODIMENTS

The present invention pertains to a novel method of inhibiting the formation of scale such as calcium scale from aqueous systems, e.g., cooling water, steam generating, gas scrubbing and pulp and papermaking systems. Specifically, the method of the present invention comprises adding to an aqueous system a modified poly[epoxysuccinic acid] of the general formula:

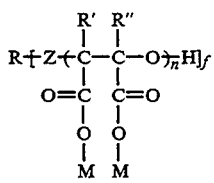

Formula I wherein R is H, a substituted or non-substituted alkyl or aryl moiety having a carbon chain up to the length where solubility in an aqueous solution is lost, or a repeat unit obtained after polymerization of an ethylenically unsaturated compound; R' and R" are hydrogen, C$_{1-4}$ alkyl or C$_{1-4}$ substituted alkyl; Z is O, S, NH, or NR, where R is as described above; n is a positive integer greater than 1; f is a positive integer; and M is hydrogen, a water soluble cation (e.g., NH$_4$+, alkali metal), or a non-substituted lower alkyl group having from 1 to 3 carbon atoms.

The polymers of the present invention can be prepared by incorporating reagents containing an α-hydroxycarboxylic acid (αHCA) functionality into a poly[epoxysuccinic acid] (PESA) polymer matrix. The αHCA compounds can be obtained by the ring opening reaction of a suitable reagent (R—[—Z—H]$_f$) with a salt or ester of epoxysuccinic acid (ESA). The αHCA compound can be synthesized prior to the incorporation reaction (Scheme A) or be generated in situ by conducting the polymerization of ESA in the presence of a suitable ring-opening reagent (Scheme B).

Scheme A
Step 1:

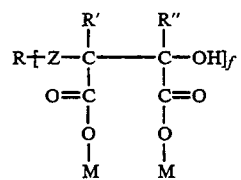

-continued
Scheme A (R, R', R", n, Z, f and M are as described above)

For a general review of ring-opening reactions of epoxides to prepare αHCA compounds, see March, "Advanced Organic Chemistry-Reactions, Mechanisms, and Structures", 2nd Edition, Chapter 10, McGraw-Hill, New York, 1977.

Methods for conducting the polymerization of ESA, Scheme A-Step 2 and Scheme B, are described by Pearson et al., U.S. Pat. No. 3,776,850 and Bush et al., U.S. Pat. No. 4,654,159, both incorporated by reference.

The reaction can be performed neat, or in aqueous or nonaqueous solvents. If the resulting product is nonaqueous it should be modified by traditional techniques known to those skilled in the art to yield a water soluble product (e.g., hydrolysis of ester derivatives).

In a preferred embodiment of the invention, aqueous solutions of the polymers of the present invention are prepared by reacting an amine with an aqueous solution of disodium epoxysuccinate (ESA.Na$_2$) in the presence of calcium hydroxide. The reaction is typically conducted under atmospheric conditions at about 30° C.-100° C., preferably from 80° C. to 100° C. The molar ratio of the ring opening reagent R —Z—H$_f$ to ESA.-Na$_2$, relative to functionality (f) may fall within the range of about 1:2 to 1:1000, with a range of 1:5 to 1:100 being preferred. The molar ratio of calcium hydroxide to ESA.Na$_2$ or ESA.Na$_2$ +αHCA may fall within the range of 1:20 to 1:3, with a ratio of 1:10 being preferred.

It will be appreciated that certain by-products (e.g., disodium tartrate, PESA, and ,βHCA compounds) may be produced along with the compounds of the present invention in the course of the above reaction schemes. The desired reaction products can be readily recovered from the reaction product by known methods; however, it is feasible and economical to employ the compounds of the present invention as produced without separation or purification.

The treatment levels of polymer added to an aqueous system can range from about 25 parts per billion to 500 parts per million of water, and preferably from about 50 parts per billion to 100 parts per million of water contained in the aqueous system to be treated. The concentration of compound necessary to provide effective calcium control will, of course, vary from system to system. The treatment level will vary, in part, with changes in temperatures and pH. However, in all cases, the concentration of modified polyepoxysuccinic acid added to an aqueous water system in accordance with the present invention is at substoichiometric concentrations. That is, the concentration of modified polyepoxysuccinic acid added is much lower than the concentration of the scale forming material in the system to be treated.

The polymers may be added directly into the desired water system in a fixed quantity and in a state of an aqueous solution, continuously or intermittently. The compounds of the present invention are also expected to exhibit corrosion inhibition and silica/silicate scale inhibition activity. In addition, the compounds of the present invention may also be used with topping agent components in order to enhance the scale controlling and corrosion inhibition properties thereof. Such topping components are readily known to those skilled in the art. Details of such compounds are disclosed by Chen, U.S. Pat. No. 4,659,481, incorporated herein by reference. It is expected that the polymers of the present invention may be used in conjunction with the polymers and topping components of Chen '481 to provide treatment programs which effectively inhibit corrosion and scale deposition in water systems.

Suitable topping agents include polyacrylates, phosphoric acid and water soluble salts thereof, phosphonic acids and water soluble salts thereof, polyvalent metal salts, azole compounds, molybdate and tungstate compounds and mixtures thereof.

A suitable polyacrylate is represented by the following formula:

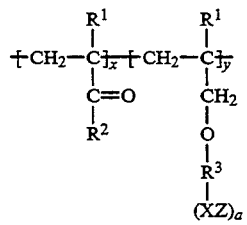

wherein $R^1$ is H or lower alkyl ($C_1$-$C_3$); $R^2$ is OH, OM or $NH_2$; M is a water soluble cation; $R^3$ is a hydroxy substituted alkyl or alkylene radical having from 1 to 6 carbon atoms or a non-substituted alkyl or alkylene radical having from 1 to 6 carbon atoms; X, when present, is an anionic radical selected from $SO_3$, $PO_3$, $PO_4$ and $CO_2$; Z, when present, i s H or any water soluble cation or cations which together counterbalance the valence of the anionic radical; a is 0 or 1, the molar ratio of x:y of the polymer being between 30:1 and 1:20.

The phosphoric acid may be orthophosphoric acid or pyrophosphoric acid or a water soluble salt thereof. The phosphonic acid may be 1-hydroxyethane-1,1-diphosphonic acid, 2-phosphonobutane- 1,2,4-tricarboxylic acid or hydroxyphosphonoacetic acid. The polyvalent metals may be $Zn^{2+}$, $Mn^{2+}$, or $Sn^{2+}$. The azole compound may be 1,2,3-tolyltriazole, benzotriazole or butylbenzotriazole. The molybdate compound may be sodium molybdate or potassium molybdate. The tungstate compound may be sodium or potassium tungstate.

The topping agents may be added to the system in an amount of about 0.01 to 500 ppm of said system.

The invention will now be further described with reference to a number of specific examples which are to be regarded solely as illustrative and not as restricting the scope of the present invention.

Example I

Preparation of aspartic acid, 3-hydroxy, N-[2-ethane sulfonic acid]-trisodium salt via Reaction Scheme A, Step 1.

A suitable reaction flask was equipped with a magnetic stirrer, reflux condenser, nitrogen sparge, thermometer, and addition parts. Taurine (99%, 12.64g, 0.1 mole) and 67 ml of deionized water were charged to the flask and sparged with nitrogen. Aqueous sodium hydroxide (50%, 8 g, 0.1 mole) was then charged to the flask to yield a clear, colorless liquid followed by ESA.$Na_2$ (90%, 20.54 g, 0.105 mole) being charged to the flask. The resulting slurry was heated at 90°±2° C. for 16.5 hours under a nitrogen atmosphere. The resulting clear solution was isolated and diluted to 130 g with deionized water.

The structure of the resulting aspartic acid, 3-hydroxy, N-[2-ethanesulfonic acid]-trisodium salt, sample reference αHCA(6), was confirmed by $^{13}C$ NMR spectroscopy. The product yield was estimated to be 93.3 mole % via integration of the methine carbons of the $^{13}C$ NMR spectrum.

Example II

Preparation of poly[oxy(1,2-dicarboxylic acid -1,2-ethanediyl)]α-hydro -ω[(ethanesulfonic acid) 2-amino]-sodium salt via Reaction Scheme A, Step 2.

To a reactor setup similar to that described in Example I was charged aqueous aspartic acid, 3-hydroxy, N-[2-ethane sulfonic acid]- trisodium salt (29.2%, 11.07 g, 0.01 mole), 48 ml deionized water, and ESA.$Na_2$ (90%, 37.16 g, 0.19 mole). The solution was sparged with nitrogen and adjusted to a pH of 10.8 with aqueous sodium hydroxide (50%). Calcium hydroxide (98%, 1.51 g, 0.02 mole) slurried in 20 ml of deionized water was then charged to the flask and the mixture was heated to 80°±2° C. for 15.5 hours. The resulting solution was then filtered, diluted to 130 g with deionized water, and collected.

The structure of the product, Sample Reference 18, was verified by $^{13}C$ NMR spectroscopy. Residual 3-hydroxy, N-[2-ethanesulfonic acid]-trisodium salt was also detected. Approximately 23.4 mole % of the ESA.$Na_2$ hydrolyzed to disodium tartrate under these reaction conditions.

Example III

Preparation of poly[oxy(1,2-dicarboxylic acid-1, 2-ethanediyl)]α-hydro -ω-[ethanesulfonic acid)2-amino]-sodium salt via Reaction Scheme B.

To a reactor setup similar to that described in Example I was charged ESA.$Na_2$ (90%, 19.56 g. 0.1 mole), 27 ml deionized water, and taurine (99%, 0.63 g, 0.005 mole). The solution was sparged with nitrogen and adjusted to a pH of 10.1 with aqueous sodium hydroxide (50%). Calcium hydroxide (98%, 0.76 g, 0.01 mole) slurried in 10 ml of deionized water was then charged to the flask and the mixture was heated at 80°±2° C. for 17 hours. The resulting solution was then filtered, diluted to 65 g with deionized water, and collected.

The $^{13}C$ NMR of the product, Sample Reference 21, was similar to that of Example II. No residual taurine was detected. Approximately 22.2 mole % of the ESA.Na$_2$ hydrolyzed to the disodium tartrate by-product under these reaction conditions.

Using the above-described preparative techniques, several other modified PESA analogs were prepared. The final products were typically a mixture of the modified PESA analog, residual αHCA, and unmodified PESA (collectively considered the "actives" portion in testing), and sodium tartrate by-product. The results of these preparations are set forth in Table I. Several αHCA analogs (Formula I, n=1) were also prepared for evaluation. These compounds are also listed in Table I for reference.

TABLE I

Modified PESA Synthesis Summary[a]

R–(Z–(CR'———CR''—O)$_n$H]$_f$
  |       |
 CO$_2$M  CO$_2$M

R' = R'' = H, M = Na, n > 1

| Sample | Mole Ratio ESA.Na$_2$:R–(Z—H]$_f$ | Composition[b] Wt. % Actives: Wt. % TA.Na$_2$ |
|---|---|---|
| | R = C$_4$H$_9$—, Z = —NH—, f = 1 | |
| αHCA[c](1) | 1.0:1.0 | |
| 1 | 20.0:1.0 | 79:21 |
| 2 | 10.0:1.0 | 77:23 |
| 3 | 6.7:1.0 | 82:18 |
| | R = C$_4$H$_9$—, Z = —O—, f = 1 | |
| αHCA(2) | 1.0:1.0 | |
| 4 | 20.0:1.0 | 82:18 |
| 5 | 10.0:1.0 | 84:16 |
| 6 | 6.7:1.0 | 85:15 |
| | R = C$_6$H$_{13}$—, Z = —NH—, f = 1 | |
| αHCA(3) | 1.0:1.0 | |
| 7 | 20.0:1.0 | 72:28 |
| 8 | 10.0:1.0 | 80:20 |
| 9 | 6.7:1.0 | 78:22 |
| | R = C$_6$H$_5$—CH$_2$—, Z = —NH—, f = 1 | |
| αHCA(4) | 1.0:1.0 | |
| 10 | 20.0:1.0 | 81:19 |
| 11 | 10.0:1.0 | 84:16 |
| | R = (HOCH$_2$CH$_2$)$_2$—, Z = \N—, f = 1 | |
| 12 | 20.0:1.0 | 80:20 |
| 13 | 10.0:1.0 | 81:19 |
| | R = (HOCH$_2$)$_3$C—, Z = —NH—, f = 1 | |
| 14 | 10.0:1.0 | 81:19 |
| | Z = NaO$_3$S— | |
| αHCA(5) | 1.0:1.0 | |
| 15 | 20.0:1.0 | 86:14 |
| 16 | 10.0:1.0 | 86:14 |
| 17 | 10.0:1.0 | 81:19 |
| | R = NaO$_3$S—CH$_2$CH$_2$—, Z = —NH—, f = 1 | |
| αHCA(6) | 1.0:1.0 | |
| 18 | 20.0:1.0 | 76:24 |
| 19 | 10.0:1.0 | 79:21 |
| 20 | 6.7:1.0 | 83:17 |
| 21 | 20.0:1.0 | 78:22 |
| 22 | 10.0:1.0 | 81:19 |
| 23 | 6.7:1.0 | 84:16 |
| | R = HOCH$_2$(CHOH)$_3$C(CO$_2$H)—, Z = —O—, f = 1 | |
| 24 | 20.0:1.0 | 78:22 |
| 25 | 10.0:1.0 | 80:20 |
| 26 | 6.7:1.0 | 83:17 |
| | R = —C(CO$_2$H)(CHOH)$_2$C(CO$_2$H)—, Z = —O—, f = 2 | |
| 27 | 20.0:1.0 | 78:22 |
| 28 | 10.0:1.0 | 81:19 |
| 29 | 6.7:1.0 | 85:15 |

TABLE I-continued

Modified PESA Synthesis Summary[a]

R–(Z–(CR'———CR''—O)$_n$H]$_f$
  |       |
 CO$_2$M  CO$_2$M

R' = R'' = H, M = Na, n > 1

| Sample | Mole Ratio ESA.Na$_2$:R–(Z—H]$_f$ | Composition[b] Wt. % Actives: Wt. % TA.Na$_2$ |
|---|---|---|
| | R = —(C$_6$H$_{12}$)—, Z = —NH—, f = 2 | |
| αHCA(7) | 1.0:1.0 | |
| 30 | 20.0:1.0 | 80:20 |
| 31 | 10.0:1.0 | 83:17 |
| 32 | 6.7:1.0 | 85:15 |
| | R = meta —CH$_2$C$_6$H$_4$—CH$_2$—, Z = —NH—, f = 2 | |
| αHCA(8) | 1.0:1.0 | |
| 33 | 20.0:1.0 | 82:18 |
| 34 | 10.0:1.0 | 83:17 |
| 35 | 6.7:1.0 | 85:15 |
| | R = para —CH$_2$—C$_6$H$_4$—CH$_2$—, Z = —NH—, f = 2 | |
| αHCA(9) | 1.0:1.0 | |
| 36 | 20.0:1.0 | 79:21 |
| 37 | 10.0:1.0 | 84:16 |
| 38 | 6.7:1.0 | 85:15 |

[a]Mole ratio of Ca(OH)$_2$: ESA.Na$_2$ + αHCA (Scheme A) or ESA.Na$_2$ (Scheme B) was 1:10 for all reactions.
[b]Reported as a weight percent of the organic solid content of the product; TA.Na$_2$ stands for disodium tartrate
[c]Corresponding αHCA analog, n = 1

EXAMPLE IV

Table II summarizes the static calcium carbonate inhibition testing of the polymers of the present invention compared to several prior art calcium carbonate control agents. The tests were performed by adding the treatment solution (sample) to a carbonate stock solution of the described conditions. A calcium stock solution was then added and the mixture was incubated for 17 hours at 70° C. All treatments were adjusted to pH 9.0 prior to use and the treatment weights, expressed as the sodium salts, accounted for the presence of disodium tartrate by-product. After cooling, a measured portion of the mixture was filtered and the filtrate pH adjusted to less than 1 with hydrochloric acid. The filtrate was then diluted and pH adjusted to 12 with sodium hydroxide. A calcium indicator, murexide, was then added and the solution titrated with a known concentration of ethylenediaminetetraacetic acid (EDTA). From titrations for the treated, stock and control solutions, the percent inhibition was calculated as follows:

$$\frac{\%}{\text{Inhibition}} = \frac{\text{mls EDTA(treated)} - \text{mls EDTA(control)}}{\text{mls EDTA(stock)} - \text{mls EDTA(control)}} \times 100$$

Typically, the test samples were evaluated twice referenced to a sample of PESA. The polymers of the present invention were in general as effective as PESA, and more effective than HEDP and PBSAM at 10 ppm actives regardless of the mole % of αHCA compound used in the synthesis. At 5 ppm actives a decrease in efficacy was observed with increasing αHCA content; however, at lower levels of HCA the activity of the polymers of the present invention generally exceeded PESA and were equivalent to that of PBSAM.

The αHCA compounds alone did not exhibit any calcium carbonate inhibition activity.

TABLE II

Static Calcium Carbonate % Inhibition Evaluation

Conditions:
1106 ppm Ca as CaCO3    Stock Solutions pH = 9.0
1160 ppm CO3 as CaCO3   Temp. = 70° C.
538 ppm Na              Duration = 17 hours
784 ppm Cl
518 ppm SO4

| Sample | 5 ppm Actives | 10 ppm Actives |
|---|---|---|
| αHCA(1) | 2.3 | 0.7 |
| 1 | 81.8 | 96.9 |
| 2 | 82.9 | 97.1 |
| 3 | 60.5 | 95.1 |
| αHCA(2) | 1.4 | 4.4 |
| 4 | 67.9 | 85.7 |
| 5 | 70.5 | 85.2 |
| 6 | 61.8 | 83.5 |
| αHCA(3) | 2.4 | 2.2 |
| 7 | 74.6 | 87.8 |
| 8 | 75.2 | 89.1 |
| 9 | 59.6 | 92.0 |
| αHCA(4) | 0.0 | 0.0 |
| 10 | 75.5 | 87.8 |
| 11 | 70.1 | 87.7 |
| 12 | 55.0 | 65.5 |
| 13 | 60.9 | 72.4 |
| 14 | 58.6 | 76.1 |
| αHCA(5) | 4.4 | |
| 15 | 56.6 | 86.3 |
| 16 | 60.0 | 85.4 |
| 17 | 74.3 | 76.8 |
| αHCA(6) | 5.1 | 3.7 |
| 18 | 77.1 | 91.3 |
| 19 | 61.5 | 89.8 |
| 20 | 44.8 | 83.0 |
| 21 | 79.6 | 96.5 |
| 22 | 58.9 | 93.2 |
| 23 | 46.6 | 83.6 |
| 24 | 66.5 | 80.6 |
| 25 | 52.7 | 80.4 |
| 26 | 43.2 | 78.8 |
| 27 | 70.1 | 82.8 |
| 28 | 59.0 | 77.9 |
| 29 | 44.3 | 77.9 |
| αHCA(7) | 6.7 | 3.3 |
| 30 | 79.2 | 91.6 |
| 31 | 75.8 | 95.4 |
| 32 | 62.0 | 92.0 |
| αHCA(8) | 0.0 | 8.3 |
| 33 | 75.9 | 91.3 |
| 34 | 80.7 | 96.5 |
| 35 | 81.0 | 98.2 |
| αHCA(9) | 1.3 | 0.9 |
| 36 | 77.7 | 91.1 |
| 37 | 80.5 | 93.0 |
| 38 | 76.0 | 96.5 |
| PESA[1] | 58.6 | 90.6 |
| PBSAM[2] | 67.5 | 76.0 |
| HEDP[3] | 73.1 | 71.3 |
| K-752[4] | 78.8 | 84.0 |
| K-732[5] | 68.4 | 74.6 |
| SCP-1[6] | 42.1 | 45.5 |

[1] PESA = Poly[2,3-oxiranedicarboxylic acid], refer to Brown et al., U.S. Pat. No. 5,062,962. Average of 12 tests.
[2] PBSAM = 2-phosphonobutane - 1,2,4-tricarboxylic acid (Mobay Chemical Co.). Average of 3 tests.
[3] HEDP = 1-hydroxyethylidene-1,1-diphosphonic acid (Monsanto Co.). Average of 5 tests.
[4] K-752 = Goodrite K-752, poly[acrylic acid](B.F. Goodrich Co.).
[5] K-732 = Goodrite K-732, poly[acrylic acid](B.F. Goodrich Co.)
[6] SCP-1 = Sulfonated copolymer; refer to Chen, U.S. Pat. No. 4,654,159

While this invention has been described with respect to particular embodiments thereof, it is apparent that numerous other forms and modifications of this invention will be obvious to those skilled in the art. The appended claims in this invention generally should be construed to cover all such obvious forms and modifications which are within the true spirit and scope of the present invention.

What is claimed is:

1. A method for controlling the formation and deposition of scale forming salts including calcium scale in an aqueous system comprising introducing into said aqueous system a sufficient amount for the purpose of a treatment comprising a modified polyepoxysuccinic acid of the general formula:

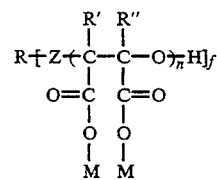

wherein R is alkyl, $C_4$-$C_9$ aryl, substituted alkyl or $C_4$-$C_9$ substituted aryl; R' and R" are each independently hydrogen, $C_{1-4}$ alkyl or $C_{1-4}$ substituted alkyl; Z is NH, NR, O or S; n is a positive integer greater than 1; f is a positive integer; and M is H, a water soluble cation or a $C_{1-3}$ alkyl group.

2. The method as recited in claim 1 further comprising adding to said aqueous system a sufficient amount for the purpose of a topping agent selected from the group consisting of polyacrylates, phosphoric acids and water soluble salts thereof, phosphonic acids and water soluble salts thereof, polyvalent metal salts and azole compounds.

3. The method as recited in claim 2 wherein said polyacrylate has the formula:

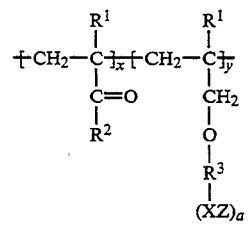

wherein each $R^1$ is independently H or lower alkyl; $R^2$ is OH, $NH_2$ or OM; M is a water soluble cation; $R^3$ is a hydroxy substituted alkyl or alkylene radical having from about 1 to 6 carbon atoms; X is $SO_3$, $PO_3$, $PO_4$ or $CO_2$; Z is H or a water soluble cation or cations; the molar ratio of x:y is from about 30:1 to 1:20; and a is 0 or 1.

4. The method as recited in claim 3 wherein said aqueous system is a cooling water system.

5. The method as recited in claim 4 wherein R is $C_1$-$C_{20}$ alkyl;

6. The method as recited in claim 4 wherein R is $C_4$-$C_6$ aryl.

7. The method as recited in claim 4 wherein R is —$CH_2C_6H_4CH_2$— and f is 2.

8. The method as recited in claim 4 wherein said modified polyepoxysuccinic acid is added to the aqueous system at active treatment levels ranging from about 25 parts per billion to about 500 parts per million.

9. The method as recited in claim 8 wherein said modified polyepoxysuccinic acid is added to the aqueous system at active treatment levels ranging from about 50 parts per billion to about 100 parts per million.

10. The method as recited in claim 3 wherein said aqueous system is a steam generating system.

11. The method as recited in claim 3 wherein said aqueous system is a gas scrubbing system.

12. The method as recited in claim 3 wherein said aqueous system is a pulp and papermaking system.

13. The method as recited in claim 1 wherein M is Na+.

14. The method as recited in claim 1 wherein R is a repeat unit obtained after polymerization of an ethylenically unsaturated compound.

15. The method as recited in claim 1 wherein said calcium scale comprises calcium carbonate scale.

* * * * *